(12) United States Patent
Koellnberger

(10) Patent No.: US 8,088,878 B2
(45) Date of Patent: Jan. 3, 2012

(54) HYDROSILYLATION REACTIONS ACTIVATED THROUGH RADIATION

(75) Inventor: Andreas Koellnberger, Marktl (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 12/863,521

(22) PCT Filed: Jan. 22, 2009

(86) PCT No.: PCT/EP2009/050715
§ 371 (c)(1),
(2), (4) Date: Jul. 19, 2010

(87) PCT Pub. No.: WO2009/092762
PCT Pub. Date: Jul. 30, 2009

(65) Prior Publication Data
US 2010/0292361 A1    Nov. 18, 2010

(30) Foreign Application Priority Data
Jan. 25, 2008    (DE) .................. 10 2008 000 156

(51) Int. Cl.
*C08G 77/08*    (2006.01)
(52) U.S. Cl. .......... 528/15; 502/158; 502/155; 502/152; 556/11

(58) Field of Classification Search .................. 556/11; 528/15; 502/158, 155, 152
See application file for complete search history.

(56) References Cited

U.S. PATENT DOCUMENTS

| 4,510,094 A | 4/1985 | Drahnak |
| 4,916,169 A * | 4/1990 | Boardman et al. .............. 522/27 |

FOREIGN PATENT DOCUMENTS

| EP | 0122008 B1 | 6/1988 |
| EP | 0146307 B1 | 9/1988 |
| EP | 0358452 A2 | 3/1990 |
| EP | 0398701 B1 | 5/1995 |
| EP | 0561893 B1 | 9/1996 |
| EP | 0561919 B1 | 2/1999 |
| EP | 0358452 B1 | 12/1999 |
| EP | 1 803 728   * | 4/2007 |
| EP | 1803728 A1 | 4/2007 |

OTHER PUBLICATIONS

Z. Xue et al., ( J. Am. Chem. Soc., 1989 111, 8779).
Magnetic Resonance in Chemistry 1992, 30, 481.

* cited by examiner

*Primary Examiner* — Margaret Moore
(74) *Attorney, Agent, or Firm* — Brooks Kushman P.C.

(57) ABSTRACT

$\eta$-cyclopentadienyl-tri($\sigma$-hydrocarbyl) platinum compounds in which the cyclopentadienyl ring is linked to a hydrolysable silyl group by an alkylene group are effective light-activated hydrosilylation catalysts which are also non-volatile.

11 Claims, No Drawings

HYDROSILYLATION REACTIONS ACTIVATED THROUGH RADIATION

CROSS-REFERENCE TO RELATED APPLICATION

This application is the U.S. national phase of PCT Appln. No. PCT/EP2009/050715 filed Jan. 22, 2009 which claims priority to German application DE 10 2008 000 156.2 filed Jan. 25, 2008.

BACKGROUND OF THE INVENTION

1. Field of the Invention

The present invention relates to novel platinum catalysts which can be activated by ultraviolet and/or visible radiation, their preparation, their use in crosslinkable silicone compositions and also the silicone elastomers produced therefrom by irradiation.

2. Description of the Related Art

In general, the crosslinking process in addition-crosslinking silicone compositions occurs via a hydrosilylation reaction in which platinum or another metal from the platinum group is usually used as catalyst. In the catalytic reaction, aliphatically unsaturated groups are reacted with Si-bonded hydrogen in order to convert the addition-crosslinkable silicone composition into the elastomeric state by formation of a network.

According to the prior art, the activation of the catalysts used is normally carried out thermally, i.e. the addition-crosslinkable silicone composition consequently has to be heated for the crosslinking process. According to the prior art, in this process, the silicone composition frequently has to be applied to a substrate, as is the case in, for example, coating processes, selected casting, molding and coextrusion or other shaping processes. The actual vulcanization process is in this case effected by means of a heating process for which costly and energy-consuming plants frequently have to be operated.

In comparison, a sometimes considerable cost saving is associated in many applications with the use of mixtures which can be crosslinked by ultraviolet and/or visible radiation. Consequently, an energy saving and process cost saving and thus a corresponding increase in productivity can be achieved. In addition, crosslinking by means of ultraviolet and/or visible radiation often allows continuous manufacture which brings further productivity advantages compared to a discontinuous batch process. A further advantage arises from the fact that, particularly in the case of multicomponent parts such as hard-soft composites which contain an elastomeric material together with, for example, a thermoplastic as the composite partner, the omission of a temperature-intensive manufacturing step prevents thermal distortion of the part.

The technical literature describes many platinum complexes which are suitable for initiating a hydrosilylation reaction by means of radiation. All platinum catalysts described can be activated by light and are also capable of crosslinking silicone compositions even after the light source is switched off. This process is known as dark reaction to those skilled in the art.

EP 0 122 008 B1 describes UV-crosslinkable silicone compositions containing a (η-diolefin)(σ-aryl)platinum complex as photosensitive catalyst. A high catalytic activity is indicated as advantageous. However, this class of catalyst nevertheless has a moderate dispersibility in the silicone matrix. In addition, the light-induced decomposition of the platinum catalyst requires the use of very short-wavelength UV-C radiation which inevitably leads to high ozone pollution in the direct vicinity of a production line.

EP 0 561 919 B1 describes a process for radiation-crosslinking hydrosilylation, in which the compositions contain not only (η-diolefin)(σ-aryl)platinum complexes but also a free-radical photoinitiator which absorbs actinic radiation and in this way contributes to an increase in the light yield. This combination of (η-diolefin)(σ-aryl)platinum complex and free-radical photoinitiator makes initiation of a hydrosilylation reaction with an accelerated crosslinking process possible. However, the use of an additional component must in principle be considered to be disadvantageous since it makes the production process correspondingly more complicated.

On the other hand, EP 0 398 701 B1 claims Pt(II)-β-diketonate complexes which have the advantage of a long pot life combined with a short gel time on illumination. However, the relatively polar compounds have the disadvantage of poor solubility in the silicone matrix and therefore have only limited suitability for many applications.

EP 0 146 307 B1 discloses ($\eta^5$-cyclopentadienyl)tri(σ-alkyl) platinum(IV) complexes which display good solubility in the silicone matrix. More highly concentrated solutions can also be achieved using the complexes. However, a considerable disadvantage of the compounds is their relatively high vapor pressure and their volatility. As a result, it is not possible to rule out a change in the platinum concentration when vacuum is applied in the production or processing of the silicone elastomer. A further consequence is that contamination of the air of the room with toxicologically problematic platinum compounds cannot be ruled out.

In EP 0 358 452 B1, sensitizers are added to the compositions containing ($\eta^5$-cyclopentadienyl)tri(σ-alkyl) platinum (IV) complexes as catalyst in order to shift the wavelength of the incoming light required for crosslinking to longer wavelengths. The advantage resulting therefrom is that the mixtures can be cured using visible light instead of ultraviolet light.

EP 0 561 893 B1 describes radiation-crosslinkable compositions containing ($\eta^5$-cyclopentadienyl)tri(σ-alkyl)platinum(IV) complexes together with a free-radical photoinitiator which absorbs actinic radiation and in this way contributes to an increase in the light yield. This combination makes an increase in the quantum yield for the mixtures used possible. The resulting increase in the dark reactivity has to be regarded as a disadvantage. In addition, the use of an additional component makes the production process more expensive and also increases the materials costs.

EP 1 803 728 A1 discloses modified ($\eta^5$-cyclopentadienyl) tri (σ-alkyl)platinum(IV) complexes which bear specific substituents (naphthyl, anthracenyl, etc.) on the cyclopentadienyl ring in order to increase the quantum yield and to shift the light wavelength required for activation to longer wavelengths. However, the attachment of aromatic rings has an adverse effect on the solubility of the complexes in the silicone matrix. These compounds, too, have the disadvantage of volatility.

Many of the platinum complexes described are also used in CVD (chemical vapor deposition) applications, which in itself indicates a high volatility of the compounds described. In the technical literature, the vapor pressure of the complexes CpPtMe$_3$ and MeCpPtMe$_3$ was determined experimentally by Z. Xue et al., (J. Am. Chem. Soc., 1989, 111, 8779). The high volatilities measured represent a not inconsiderable risk from many points of view, especially because of the danger of platinum contamination of the working area. In addition, inhalation of the platinum compounds can also represent a health risk. In addition, the ability of the relatively small, nonpolar molecules to pass through the skin, which is attributable to the chemical structure, has to be considered to be a further not inconsiderable disadvantage of the platinum complexes described.

In summary, it can be said that none of the silicone compositions known hitherto which can be crosslinked by means of visible and/or UV radiation satisfactorily fulfill the requirements which have to be met by such silicone compositions which are employed, in particular, for production in an industrial environment.

SUMMARY OF THE INVENTION

It was therefore an object of the present invention to provide suitable platinum catalysts. A further object of the present invention was to provide silicone compositions which do not have the abovementioned disadvantages. These and other objects are achieved by the use of (η-cyclopentadienyl)-tri(hydrocarbyl) platinum complexes bearing a hydrolysable silyl group bonded to the cyclopentadiene ring via an alkylene group.

The present patent application provides a platinum compound of the general formula (I)

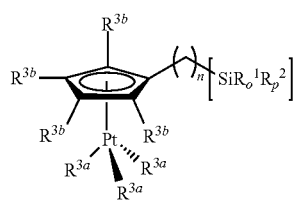

(I)

where
n=1 to 8,
o=0 to 2,
p=1 to 3,
the radicals $R^1$ are identical or different and are each, independently of one another, a monovalent, unsubstituted or substituted, linear, cyclic or branched hydrocarbon radical which contains aliphatically saturated or unsaturated or aromatically unsaturated radicals and from 1 to 30 carbon atoms and in which individual carbon atoms may be replaced by O, N, S or P atoms,
the radicals $R^2$ are identical or different and are each, independently of one another, hydrolyzable functional groups selected from the group consisting of
　carboxy —O—C(O)$R^4$,
　oxime —O—N=C$R^4{}_2$,
　alkoxy —O$R^4$,
　alkenyloxy —O—$R^6$,
　amide —N$R^4$—C(O)$R^5$,
　amine —N$R^4R^5$,
　aminoxy —O—N$R^4R^5$, and silicon in the formula is tetravalent where
　the radicals $R^4$ are identical or different and are each, independently of one another, H, alkyl, aryl, arylalkyl, alkylaryl,
　the radicals $R^5$ are identical or different and are each, independently of one another, alkyl, aryl, arylalkyl, alkylaryl,
　$R^6$ is a linear or branched, aliphatically unsaturated organic radical, the radicals $R^{3a}$ are identical or different and are each, independently of one another, alkyl, aryl, arylalkyl, alkylaryl having from 1 to 30 carbon atoms, where the hydrogens may be substituted by -Hal or —Si$R_3{}^3$, where
the radicals $R^3$ are identical or different and are each, independently of one another, a monovalent, unsubstituted or substituted, linear, cyclic or branched hydrocarbon radical,
the radicals $R^{3b}$ are identical or different and are each, independently of one another, hydrogen or a monovalent, unsubstituted or substituted, linear or branched hydrocarbon radical which contains aliphatically saturated or unsaturated or aromatically unsaturated radicals and has from 1 to 30 carbon atoms and in which individual carbon atoms may be replaced by O, N, S or P atoms and which together with the cyclopentadienyl radical may form fused rings.

Preferred radicals $R^1$ are linear saturated hydrocarbon radicals having from 1 to 8 carbon atoms. Particular preference is given to the phenyl radical.

Preferred radicals $R^2$ are methoxy, ethoxy, acetoxy and 2-methoxyethoxy groups.

Preferred radicals $R^{3a}$ are linear and branched, substituted or unsubstituted alkyl radicals such as methyl, ethyl, propyl or butyl radicals.

Preferred radicals $R^{3b}$ are linear and branched, substituted or unsubstituted linear alkyl radicals such as methyl, ethyl, propyl or butyl radicals. Particular preference is given to fused rings which may be further substituted, for example the indenyl or fluorenyl radical.

Examples of monomeric platinum compounds having the structure (I) are given hereinbelow, where each of the variations mentioned below can be combined with one another in any way and the choice is not restricted to the examples.

Examples of the variation of the alkyl spacer between the cyclopentadienyl group and the silyl unit:
trimethyl[(trimethoxysilyl)methylcyclopentadienyl]platinum(IV)
trimethyl[(2-trimethoxysilyl)ethylcyclopentadienyl]platinum(IV)
trimethyl[(3-trimethoxysilyl)propylcyclopentadienyl]platinum(IV)
trimethyl[(4-trimethoxysilyl)butylcyclopentadienyl]platinum(IV)
trimethyl[(5-trimethoxysilyl)pentylcyclopentadienyl]platinum (IV)
trimethyl[(6-trimethoxysilyl)hexylcyclopentadienyl]platinum(IV)
trimethyl[(7-trimethoxysilyl)heptylcyclopentadienyl]platinum(IV)
trimethyl[(8-trimethoxysilyl)octylcyclopentadienyl]platinum(IV)
trimethyl[(9-trimethoxysilyl)nonylcyclopentadienyl]platinum (IV)
trimethyl[(10-trimethoxysilyl)decylcyclopentadienyl]platinum(IV)
trimethyl[(11-trimethoxysilyl)undecylcyclopentadienyl]platinum(IV)
trimethyl[(12-trimethoxysilyl)dodecylcyclopentadienyl]platinum(IV)
trimethyl[(13-trimethoxysilyl)tridecylcyclopentadienyl]platinum(IV)
trimethyl[(14-trimethoxysilyl)tetradecylcyclopentadienyl]platinum(IV)
trimethyl[(15-trimethoxysilyl)pentadecylcyclopentadienyl]platinum(IV)
trimethyl[(16-trimethoxysilyl)hexadecylcyclopentadienyl]platinum(IV)

trimethyl[(17-trimethoxysilyl)heptadecylcyclopentadienyl]platinum(IV)
trimethyl[(18-trimethoxysilyl)octadecylcyclopentadienyl]platinum(IV)
trimethyl[(2-trimethoxysilyl)-1-methylethylcyclopentadienyl]platinum(IV)
trimethyl[(3-trimethoxysilyl)-2-methyl-2-propylcyclopentadienyl]platinum(IV)

Examples of the variation of the groups on the silyl radical:
trimethyl[(triethoxysilyl)methylcyclopentadienyl]platinum (IV)
trimethyl[(tripropoxysilyl)methylcyclopentadienyl]platinum(IV)
trimethyl[(triacetoxysilyl)methylcyclopentadienyl]platinum (IV)
trimethyl[(triisopropenoxysilyl)methylcyclopentadienyl]platinum(IV)
trimethyl[(tridimethylaminesilyl)methylcyclopentadienyl]platinum(IV)
trimethyl[(triethoxysilyl)methylcyclopentadienyl]platinum (IV)
trimethyl[(2-triethoxysilyl)ethylcyclopentadienyl]platinum (IV)
trimethyl[(3-triethoxysilyl)propylcyclopentadienyl]platinum(IV)
trimethyl[(8-triethoxysilyl)octylcyclopentadienyl]platinum (IV)
trimethyl[(methyldimethoxysilyl))methylcyclopentadienyl]platinum(IV)
trimethyl[(dimethylmethoxysilyl))methylcyclopentadienyl]platinum(IV)
trimethyl[(methyldiethoxysilyl))methylcyclopentadienyl]platinum(IV)
trimethyl[(dimethylethoxysilyl))methylcyclopentadienyl]platinum(IV)
trimethyl[(methyldiacetoxysilyl))methylcyclopentadienyl]platinum(IV)
trimethyl[(dimethylacetoxysilyl))methylcyclopentadienyl]platinum(IV)
trimethyl[(methylbisisopropenoxysilyl))methylcyclopentadienyl]platinum(IV)
trimethyl[(dimethylisopropenoxysilyl))methylcyclopentadienyl]platinum(IV)
trimethyl[(ethyldimethoxysilyl))methylcyclopentadienyl]platinum(IV)
trimethyl[(diethylethoxysilyl))methylcyclopentadienyl]platinum(IV)
trimethyl[(ethyldiethoxysilyl))methylcyclopentadienyl]platinum(IV)
trimethyl[(diethylmethoxysilyl))methylcyclopentadienyl]platinum(IV)
trimethyl[(ethyldiacetoxysilyl))methylcyclopentadienyl]platinum(IV)
trimethyl[(diethylacetoxysilyl))methylcyclopentadienyl]platinum(IV)
trimethyl[(ethylbisisopropenoxysilyl))methylcyclopentadienyl]platinum(IV)
trimethyl[(diethylisopropenoxysilyl))methylcyclopentadienyl]platinum(IV)
trimethyl[(propyldimethoxysilyl))methylcyclopentadienyl]platinum (IV)
trimethyl[(dipropylethoxysilyl))methylcyclopentadienyl]platinum(IV)
trimethyl[(propyldiethoxysilyl))methylcyclopentadienyl]platinum(IV)
trimethyl[(dipropylmethoxysilyl))methylcyclopentadienyl] platinum (IV)
trimethyl[(propyldiacetoxysilyl))methylcyclopentadienyl]platinum (IV)
trimethyl[(dipropylacetoxysilyl))methylcyclopentadienyl]platinum (IV)
trimethyl[(propylbisisopropenoxysilyl))methylcyclopentadienyl]platinum(IV)
trimethyl[(dipropylisopropenoxysilyl))methylcyclopentadienyl]platinum(IV)
trimethyl[(octyldimethoxysilyl))methylcyclopentadienyl] platinum (IV)
trimethyl[(dioctylethoxysilyl))methylcyclopentadienyl]platinum(IV)
trimethyl[(octyldiethoxysilyl))methylcyclopentadienyl]platinum(IV)
trimethyl[(dioctylmethoxysilyl))methylcyclopentadienyl]platinum(IV)
trimethyl[(octyldiacetoxysilyl))methylcyclopentadienyl]platinum(IV)
trimethyl[(dioctylacetoxysilyl))methylcyclopentadienyl]platinum(IV)
trimethyl[(octylbisisopropenoxysilyl))methylcyclopentadienyl]platinum(IV)
trimethyl[(dioctylisopropenoxysilyl))methylcyclopentadienyl]platinum(IV)
trimethyl[(isooctyldimethoxysilyl))methylcyclopentadienyl]platinum(IV)
trimethyl[(diisooctylethoxysilyl))methylcyclopentadienyl]platinum(IV)
trimethyl[(isooctyldiethoxysilyl))methylcyclopentadienyl]platinum(IV)
trimethyl[(diisooctylmethoxysilyl))methylcyclopentadienyl]platinum(IV)
trimethyl[(isooctyldiacetoxysilyl))methylcyclopentadienyl]platinum(IV)
trimethyl[(diisooctylacetoxysilyl))methylcyclopentadienyl]platinum(IV)
trimethyl[(isooctylbisisopropenoxysilyl))methylcyclopentadienyl]platinum (IV)
trimethyl[(diisooctylisopropenoxysilyl))methylcyclopentadienyl]platinum (IV)

Examples of the variation of groups bound to platinum:
triethyl[(trimethoxysilyl)methylcyclopentadienyl]platinum (IV)
tripropyl[(trimethoxysilyl)methylcyclopentadienyl]platinum(IV)
tributyl[(trimethoxysilyl)methylcyclopentadienyl]platinum (IV)
tripentyl[(trimethoxysilyl)methylcyclopentadienyl]platinum (IV)
trineopentyl[(trimethoxysilyl)methylcyclopentadienyl]platinum(IV)
trihexyl[(trimethoxysilyl)methylcyclopentadienyl]platinum (IV)
triheptyl[(trimethoxysilyl)methylcyclopentadienyl]platinum (IV)
trioctyl[(trimethoxysilyl)methylcyclopentadienyl]platinum (IV)
triisooctyl[(trimethoxysilyl)methylcyclopentadienyl]platinum(IV)
tris(trimethylsilylmethyl)[(trimethoxysilyl)methyl-cyclopentadienyl]platinum(IV)

Examples of mixed variations:
trimethyl[(methyldimethoxysilyl)propylcyclopentadienyl] platinum (IV)
trimethyl[(methyldimethoxysilyl)propylmethylcyclopentadienyl]platinum(IV)

trimethyl[(methyldimethoxysilyl)propyltetramethylcyclopentadienyl]platinum(IV)
trimethyl[(dimethylmethoxysilyl)propylcyclopentadienyl]platinum(IV)
trimethyl[(dimethylethoxysilyl)propylcyclopentadienyl]platinum(IV)
trimethyl[(methyldiethoxysilyl)propylmethylcyclopentadienyl]platinum(IV)
trimethyl[(triethoxysilyl)propylcyclopentadienyl]platinum(IV)
trimethyl[(methyldimethoxysilyl)octylcyclopentadienyl]platinum(IV)
trimethyl[(methyldimethoxysilyl)octylmethylcyclopentadienyl]platinum(IV)
trimethyl[(methyldimethoxysilyl)octyltetramethylcyclopentadienyl]platinum(IV)
trimethyl[(dimethylmethoxysilyl)octylcyclopentadienyl]platinum(IV)
trimethyl[(dimethylethoxysilyl)octylcyclopentadienyl]platinum(IV)
trimethyl[(methyldiethoxysilyl)octylmethylcyclopentadienyl]platinum(IV)

Platinum compounds having the structure (I) are specially prepared platinum complexes. The process for preparing the platinum compound of the general formula (I) is carried out by reacting a platinum precursor, which is, if appropriate, prepared in situ by alkylation of a Pt(IV) salt in a preceding step, with a monomeric cyclopentadienylalkylsilane containing at least one hydrolyzable group in an aprotic solvent at temperatures of from −78° C. to 100° C.

The synthesis methods and purification methods are based on methods known to those skilled in the art.

The platinum precursor can be, for example, $(Me_3PtI)_4$, $(Me_3PtBr)_4$ or $(Me_3PtCl)_4$ and is reacted with a monomeric cyclopentadienylalkylsilane bearing at least one hydrolyzable group. The synthesis is carried out by a method analogous to published processes known from the prior art, for example in Magnetic Resonance in Chemistry 1992, 30, 481 or in J. Am. Chem. Soc 1989, 111, 8779. The cyclopentadienyl-functionalized silane can be deprotonated by means of strong bases such as LiH, NaH, KH, n-butyllithium or t-butyllithium and thus be present in activated form as cyclopentadienyl anion before reaction with the platinum precursor. The reaction is carried out in an aprotic solvent such as diethyl ether, tetrahydrofuran, furan, ethyl acetate or methyl acetate at temperatures of from −78° C. to 100° C. After the reaction is complete, solvent is taken off and the platinum complex is purified by distillation, crystallization, chromatography or other customary methods known from the prior art.

Platinum compounds of the general formula (I) have the advantage over the systems used hitherto that in the monomeric state they bear, in the molecule, hydrolyzable groups which after appropriate purification can be crosslinked or condensed into a siloxane matrix without the platinum complex being destroyed in the process. It follows that the catalyst can be bound to an organosilicon monomer, oligomer or polymer without the catalyst being prematurely activated for the hydrosilylation reaction. The preparation of the monomeric compounds in high purity by conventional techniques and the subsequent bonding to the siloxane matrix reduces both the vapor pressure and the bioavailability of the catalyst from the silicone matrix both in uncrosslinked silicone mixtures and in crosslinked silicone mixtures. Examples of conventional purification techniques are distillation, sublimation, crystallization, chromatography and extraction. In addition, the high purity of the monomeric platinum compounds also allows in principle the production of one-component mixtures. The compositions of the invention can be either one-component silicone compositions or two-component silicone compositions. In the latter case, the two components of the compositions according to the invention can contain all constituents in any ratios.

The present patent application further provides platinum catalysts (D) of the general formula (II)

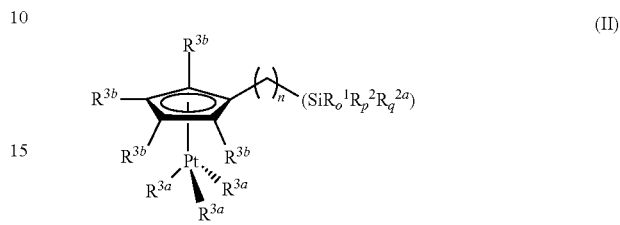

(II)

where
$R^1$, $R^2$, $R^3$, $R^{3a}$ and $R^{3b}$, n, o, p are as defined above,
q=1 to 3, and
the radicals $R^{2a}$ are identical or different and are each, independently of one another, a monovalent, linear, cyclic or branched, monomeric, oligomeric or polymeric organosilicon radical which can contain
  aliphatically saturated groups which have from 1 to 30 carbon atoms and in which individual carbon atoms may be replaced by Hal, O, N, S or P atoms and/or
  aliphatically unsaturated groups which have from 1 to 30 carbon atoms and in which individual carbon atoms may be replaced by Hal, O, N, S or P atoms and/or
  aromatic groups which have from 1 to 30 carbon atoms and in which individual carbon atoms may be replaced by Hal, O, N, S or P atoms and/or
  Si-bonded hydrogen atoms
  and/or hydroxyl groups
  and/or hydrolyzable groups.

Preferred radicals $R^{2a}$ are linear oligodimethylsiloxy and polydimethylsiloxy radicals which have a chain length of from 1 to 5000 and bear hydroxy, trimethylsilyl, dimethylsilyl or vinyl end groups. Preference is also given to using linear oligodimethylsiloxy and polydimethylsiloxy radicals which have a chain length of from 1 to 5000 and contain phenylmethylsiloxy units or diphenylsiloxy units. Further preference is given to branched and network-like oligosiloxy or polysiloxy radicals which additionally contain trifunctional or tetrafunctional units. In addition, resins and pyrogenic silicas are also preferred as radicals $R^{2a}$.

The platinum compound of the general formula (I) is not used directly as hydrosilylation catalyst in silicone mixtures but is instead bound to the siloxane chain by cohydrolysis with suitable OH-, OR- or Hal-functionalized monomeric, oligomeric or polymeric organosilicon compounds.

The organosilicon compound preferably comprises units of the general formula (III),

(III)

where
the radicals $R^{20}$ are identical or different and are each a monovalent, SiC-bonded, substituted or unsubstituted hydrocarbon radical having from 1 to 18 carbon atom(s) per radical,
the radicals $R^{21}$ are identical or different and are each a monovalent, SiC-bonded, substituted or unsubstituted aromatic hydrocarbon radical having from 6 to 30 carbon atoms, the radicals X are identical or different and are each a halogen atom, a hydrogen atom, a hydroxy group or a radical of the formula —R2, where R2 is a hydrolyzable group having the meaning indicated above, $0 \leq j \leq 3$,
$0 \leq k \leq 3$,
$0 \leq l \leq 3$, with the proviso that the sum j+k+l is $\leq 3$.

Examples of suitable organosilicon compounds of the general formula (III) are: dimethyldichlorosilane, dimethyldimethoxysilane, dimethylsilanediol, methyl-trimethoxysilane, vinyltrimethoxysilane, vinyl-tris(dimethylsiloxy)silane, 3-chloropropyltriethoxysilane, 3-chloropropyldimethylmethoxysilane, dodecyl-methyldiethoxysilane, n-octadecyltrimethoxysilane, hexamethoxydisilane, 1,1,3,3-tetraethoxy-1,3-dimethyl-disiloxane, 1,1,3,3-tetrachloro-1,3-disilabutane, 1,1,3,3-tetramethyl-1,3-diethoxydisiloxane, α,ω-silanol-terminated polydimethylsiloxanes [CAS 70131-67-8], α,ω-silanol-terminated diphenylsiloxane-dimethyl-siloxane copolymers [CAS 68951-93-9, 68083-14-7], α,ω-silanol-terminated polydiphenylsiloxanes [CAS 63148-59-4], α,ω-silanol-terminated polytrifluoro-propylmethylsiloxanes [CAS 68607-77-2], silanol-trimethylsilyl-modified Q resins [CAS 56275-01-5].

For the cohydrolysis, it is possible to use catalysts known to those skilled in the art, for example acids, alkalis, Zn compounds, Al compounds or Sn compounds, e.g. bis(2,4-pentanedionato)zinc, aluminum tris(2,4-pentanedionate), butyllithium, t-butyllithium, trifluoroacetic acid, acetic acid. This significantly reduces the volatility compared to Me$_3$Pt derivatives having a low degree of substitution, which leads to a significantly lower bioavailability in the case of incorporation. The platinum complexes according to the invention consequently have significantly improved safety during handling and a far lower vapor pressure.

The platinum catalysts (D) according to the invention preferably have a molecular weight of at least 500 g/mol.

The platinum catalysts (D) of the invention are useful as catalysts for hydrosilylation reactions, for the hydrogenation of unsaturated compounds, for polymerization reactions, in which activation is effected by means of ultraviolet or visible radiation. Examples are the hydrosilylation reaction in organosilicon chemistry known from the literature, as catalyst for the hydrogenation of unsaturated organic compounds or polymers and for oligomerization of acetylenes and other alkynes.

A significant advantage of the platinum catalysts (D) of the invention is the possibility of subsequently crosslinking the catalyst into the silicone matrix, in which the ligand structure of the platinum and the reactivity remain unchanged. In the monomeric state, hydrolyzable groups which allow condensation into the silicone matrix by simple methods known to those skilled in the art without the catalyst (D) having to be activated prematurely for the hydrosilylation reaction are present in the molecule. There is in principle a theoretical possibility of achieving bonding to Si—H crosslinkers by means of a hydrosilylation reaction by introduction of vinyl groups into the monomeric platinum catalyst and thus of binding a catalyst which is possibly not activated by radiation into the crosslinked mixture, but this requires a previously activated platinum catalyst. Evaporation of the catalyst from uncrosslinked mixtures cannot be prevented in this way. To prevent evaporation in both uncrosslinked and crosslinked silicone mixtures, it is necessary to bond the catalyst to the silicone polymer by means of a reaction which does not require an active hydrosilylation catalyst. In this way, it is also possible to manufacture one-component mixtures.

The invention further provides addition-crosslinking silicone rubber compositions, comprising
(i) at least one compound selected from the group consisting of the compounds (A), (B) and (C), where
    (A) is an organic compound and/or an organosilicon compound containing at least two radicals having aliphatic carbon-carbon multiple bonds,
    (B) is an organosilicon compound containing at least two Si-bonded hydrogen atoms, and
    (C) is an organosilicon compound containing SiC-bonded radicals having aliphatic carbon-carbon multiple bonds and Si-bonded hydrogen atoms,
    with the proviso that the composition contains at least one compound having aliphatic carbon-carbon multiple bonds and at least one compound having Si-bonded hydrogen atoms, and
(ii) at least one platinum catalyst (D).

The compounds (A), (B) and (C) used in the compositions of the invention are selected according to the prior art in such a way that they can be converted into a crosslinked state. Thus, for example, compound (A) has at least two aliphatically unsaturated radicals and (B) has at least three Si-bonded hydrogen atoms, or compound (A) has at least three aliphatically unsaturated radicals and siloxane (B) has at least two Si-bonded hydrogen atoms, or a siloxane (C) which has aliphatically unsaturated radicals and Si-bonded hydrogen atoms is used instead of compound (A) and (B) so that crosslinking of the components can take place. In addition, mixtures of (A), (B) and (C) having aliphatically unsaturated radicals and Si-bonded hydrogen atoms are possible.

The ratio of the components (A), (B) and (C) corresponds to those known from the prior art. The platinum catalyst (D) is used in such amounts that, based on the Pt(0) content, the catalyst amounts known from the prior art are likewise present in the composition of the invention.

The compound (A) can be a silicon-free organic compound preferably having at least two aliphatically unsaturated groups or an organosilicon compound preferably having at least two aliphatically unsaturated groups or else a mixture thereof.

Examples of silicon-free organic compounds (A) are 1,3,5-trivinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]hepta-2,5-diene, 1,3-diisopropenylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methyl-1,5-heptadiene, 3-phenyl-1,5-hexadiene, 3-vinyl-1,5-hexadiene and 4,5-dimethyl-4,5-diethyl-1,7-octa-diene, N,N'-methylenebisacrylamide, 1,1,1-tris(hydroxy-methyl)propane triacrylate, 1,1,1-tris(hydroxy-methyl)propane trimethacrylate, tripropylene glycol diacrylate, diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6(1H,3H,5H)trione, diallyl malonate, polyethylene glycol diacrylate, polyethylene glycol dimethacrylate, poly(propylene glycol) methacrylate.

The silicone compositions of the invention preferably contain at least one aliphatically unsaturated organosilicon compound as constituent (A); it is here possible to use all aliphatically unsaturated organosilicon compounds which have hitherto been used in addition-crosslinking compositions, for example silicone block copolymers having urea segments, silicone block copolymers having amide segments and/or imide segments and/or ester-amide segments and/or polystyrene segments and/or silarylene segments and/or carborane segments and silicone graft copolymers having ether groups.

If (A) is an organosilicon compound having SiC-bonded radicals having aliphatic carbon-carbon multiple bonds, preference is given to linear or branched organopolysiloxanes made of units of the general formula (IV)

$$R^7_a R^8_b SiO_{(4-a-b)/2} \quad (IV),$$

where
R$^7$ is a hydroxyl radical or a monovalent, optionally halogen-substituted hydrocarbon radical which has from 1 to 20 carbon atoms and is free of aliphatically unsaturated groups and may contain O, N, S or P atoms,
R$^8$ is a monovalent, aliphatically unsaturated, optionally halogen-substituted hydrocarbon radical which has from 2 to 10 carbon atoms and may contain O, N, S or P atoms,
b is from 0.0001 to 2,
with the proviso that $1.5 < (a+b) \leq 3.0$ and that an average of at least two aliphatically unsaturated radicals R$^8$ are present per molecule and that the viscosity determined at 25° C. of the diorganopolysiloxanes (A) is from 1 to 40,000,000 mPa*s.

Organosilicon compounds (B) containing Si—H-bonded hydrogen atoms are preferably linear or branched organopolysiloxanes made up of units of the general formula (V)

$$R^9_c R^{10}_d R^{11}_e H_f SiO_{(4-c-d-2e-f)/2}$$

where
R$^9$ is a monovalent aliphatically unsaturated hydrocarbon radical having from 1 to 20 carbon atoms,
R$^{10}$ is (a) a monovalent, unsubstituted or halogen-substituted hydrocarbon radical which has from 6 to 15 carbon atoms and contains at least one aromatic C$_6$ ring or (b) a monovalent, unsubstituted or halogen-substituted, saturated hydrocarbon radical which has from 2 to 20 carbon atoms and in which individual carbon atoms may be replaced by O, N, S or P atoms,
R$^{11}$ is a divalent, unsubstituted or halogen-substituted hydrocarbon radical which is Si-bonded at both ends and has from 6 to 20 carbon atoms and in which individual carbon atoms may be replaced by O, N, S or P atoms,
c and f are positive numbers and
d and e are each zero or a positive number, with the proviso that the sum (c+d+2e+f) is $\leq 3$, the organohydrogenpolysiloxane (B) contains an average of at least 3 SiH groups per molecule, and
that the viscosity determined at 25° C. of the organohydrogenpolysiloxane (B) is from 5 mPa·s to 50,000 mPa·s.

Examples of radicals R$^7$ are alkyl radicals such as methyl, ethyl, propyl, isopropyl, tert-butyl, n-pentyl, isopentyl, neopentyl, tert-pentyl, n-octyl, 2-ethylhexyl, 2,2,4-trimethylpentyl, n-nonyl and octadecyl radicals; cycloalkyl radicals such as the cyclopentyl, cyclohexyl, cycloheptyl, norbornyl, adamantylethyl or bornyl radicals; aryl or alkaryl radicals such as the phenyl, ethylphenyl, tolyl, xylyl, mesityl and naphthyl radicals; aralkyl radicals such as the benzyl, 2-phenylpropyl and phenylethyl radicals, and also derivatives of the above radicals which are halogenated or functionalized by organic groups, e.g. the 3,3,3-trifluoropropyl, 3-iodopropyl, 3-isocyanatopropyl, aminopropyl, methacryloyloxymethyl or cyanoethyl radical. Preferred radicals R$^7$ contain from 1 to 10 carbon atoms and optionally halogen substituents. Particularly preferred radicals R$^7$ are the methyl, phenyl and 3,3,3-trifluoropropyl radicals, in particular the methyl radical.

The radicals R$^8$ can undergo a hydrosilylation reaction. Examples are alkenyl and alkynyl radicals such as the vinyl, allyl, isopropenyl, 3-butenyl, 2,4-pentadienyl, butadienyl, 5-hexenyl, undecenyl, ethynyl, propynyl and hexynyl radicals; cycloalkenyl radicals such as the cyclopentenyl, cyclohexenyl, 3-cyclohexenylethyl, 5-bicycloheptenyl, norbornenyl, 4-cyclooctenyl or cyclooctadienyl radical; alkenylaryl radicals such as the styryl or styrylethyl radical, and also halogenated and heteroatom-containing derivatives of the above radicals, e.g. the 2-bromovinyl, 3-bromo-1-propynyl, 1-chloro-2-methylallyl, 2-(chloromethyl)allyl, styryloxy, allyloxypropyl, 1-methoxyvinyl, cyclopentenyloxy, 3-cyclohexenyloxy, acryloyl, acryloyloxy, methacryloyl and methacryloyloxy radicals. Preferred radicals R$^8$ are the vinyl, allyl and 5-hexenyl radicals, in particular the vinyl radical.

The viscosity of the diorganopolysiloxanes (A) of the general formula (IV), determined at 25° C., is preferably in the range from 1 to 40,000,000 mPa·s. Depending on the type of the self-adhesive addition-crosslinking silicone composition of the invention, various viscosity ranges are preferred for the diorganopolysiloxanes (A). In the case of the compositions known as RTV-2 (room temperature vulcanizing), viscosities of from 100 to 10 000 mPa*s are particularly preferred, in the case of LSR (liquid silicone rubber) viscosities of from 1000 to 500,000 mPa·s are particularly preferred and in the case of HTV (high temperature vulcanizing) compositions viscosities of from 2000 to 40,000 mPa·s are particularly preferred. The molecular weight of the constituent (A) can vary within wide limits, for instance in the range from $10^2$ to $10^6$ g/mol. Thus, the constituent (A) can be, for example, a relatively low molecular weight alkenyl-functional oligosiloxane such as 1,2-divinyltetramethyldisiloxane, but can also be a highly polymeric polydimethylsiloxane, for example having a molecular weight of $10^5$ g/mol (number average determined by means of NMR), having lateral or terminal Si-bonded vinyl groups. The structure of the molecules forming the constituent (A) is also not fixed; in particular, the structure of a relatively high molecular weight, i.e. oligomeric or polymeric, siloxane can be linear, cyclic, branched or else resin-like, network-like. Of course, it is also possible to use mixtures of different siloxanes which satisfy the criteria of constituent (A).

As organosilicon compound (B), it is possible to use all hydrogen-functional organosilicon compounds which are useful in addition-crosslinkable compositions. The molecular weight of the constituent (B) can likewise vary within wide limits, for instance in the range from $10^2$ to $10^6$ g/mol. Thus, the constituent (B) can be, for example, a relatively low molecular weight SiH-functional oligosiloxane such as tetramethyldisiloxane but can also be a highly polymeric polydimethylsiloxane having lateral or terminal SiH groups or a silicone resin having SiH groups.

The structure of the molecules forming the constituent (B) is also not fixed; in particular, the structure of a relatively high molecular weight, i.e. oligomeric or polymeric, SiH-containing siloxane can be linear, cyclic, branched or else resin-like, network-like. Linear and cyclic polysiloxanes (B) are preferably composed of units of the formulae $R^9_3SiO_{1/2}$, $HR^9_2SiO_{1/2}$, $HR^9SiO_{2/2}$ and $R^9_2SiO_{2/2}$, where R$^9$ is as defined above. Branched and network-like polysiloxanes additionally contain trifunctional and/or tetrafunctional units, with preference being given to units of the formulae $R^9SiO_{3/2}$, $HSiO_{3/2}$ and $SiO_{4/2}$, where R$^9$ is as defined above.

Examples of R$^9$ are alkyl radicals such as the methyl, ethyl, propyl, isopropyl, tert-butyl, n-octyl, 2-ethylhexyl and octadecyl radicals and also cycloalkyl radicals such as the cyclopentyl, cyclohexyl, norbornyl and bornyl radicals. Preferred radicals $R^9$ are hydrocarbons having from 1 to 10 carbon atoms. A particularly preferred radical $R^9$ is the methyl radical.

Examples of $R^{10}$ are the phenyl, tolyl, xylyl, biphenylyl, anthryl, indenyl, phenanthryl, naphthyl, benzyl, phenylethyl, and phenylpropyl radicals and also derivatives of these radicals which are functionalized with organic groups or are halogenated, e.g. o-, m-, p-chlorophenyl, pentafluorophenyl, bromotolyl, trifluorotolyl, phenoxy, benzyloxy, benzyloxyethyl, benzoyl, benzoyloxy, p-tert-butylphenoxypropyl, 4-nitrophenyl, quinolinyl and pentafluorobenzoyloxy radicals.

Examples of hydrocarbon radicals $R^{10}$ (b) having from 2 to 20 carbon atoms are radicals such as 3-chloropropyl, 3-bromopropyl, 3,3,3-trifluoropropyl, 2-fluoroethyl, 1,1-dihydroperfluorododecyl and 2-cyanoethyl. Preferred radicals $R''$ are the phenyl radical and the 3,3,3-tri-fluoropropyl radical. A particularly preferred radical $R^{10}$ is the phenyl radical.

Preferred radicals $R^{11}$ have the general formula (VI)

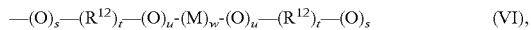

where
  s, t, u and w are each, independently of one another, 0, 1 or 2,
  the radicals $R^{12}$ can be identical or different and are each, independently of one another, a divalent, unsubstituted or halogen-substituted hydrocarbon radical which has from 1 to 10 carbon atoms and is free of aliphatically unsaturated groups and in which individual carbon atoms may be replaced by O, N, S or P atoms, for example —CH$_2$—, —CH$_2$—CH$_2$—, —CH$_2$—CH$_2$—CH$_2$—, —CF$_2$—, —CH$_2$—CF$_2$—, —CH$_2$—CH(CH$_3$)—, —C(CH$_3$)$_2$—, —CH$_2$—C(CH$_3$)$_2$—, —C(CH$_3$)$_2$—CH$_2$—, CH$_2$—CH$_2$—O— or —CF$_3$CF$_2$—O—, and
  M is a bivalent radical such as -Ph-, -Ph-O-Ph-, -Ph-S-Ph-, -Ph-SO$_2$-Ph-, -Ph-C(CH$_3$)$_2$-Ph-, -Ph-C(CF$_3$)$_2$-Ph-, -Ph-C(O)-Ph-, cyclohexylene or norbornylene, where Ph is a phenylene group.

It is also possible to use mixtures of different siloxanes which satisfy the criteria of constituent (B). In particular, the molecules forming the constituent (B) may also contain aliphatically unsaturated groups in addition to the obligatory SiH groups. Particular preference is given to using low molecular weight SiH-functional compounds such as tetrakis(dimethylsiloxy)silane and tetramethylcyclo-tetrasiloxane and also relatively high molecular weight, SiH-containing siloxanes such as poly(hydrogenmethyl)siloxanes and poly(dimethylhydrogenmethyl)siloxanes having viscosities at 25° C. of from 10 to 10,000 mPa·s, or analogous SiH-containing compounds in which part of the methyl groups has been replaced by 3,3,3-trifluoropropyl or phenyl groups.

Constituent (B) is preferably present in the crosslinkable silicone compositions of the invention in such an amount that the molar ratio of SiH groups to aliphatically unsaturated groups of (A) is from 0.1 to 20, more preferably in the range from 1.0 to 5.0.

The components (A) and (B) used according to the invention are commercial products or can be prepared by processes customary in chemistry.

Instead of components (A) and (B), the silicone compositions of the invention can contain organopolysiloxanes (C) which have both aliphatic carbon-carbon multiple bonds and Si-bonded hydrogen atoms. The silicone compositions of the invention can also contain all three components (A), (B) and (C).

If siloxanes (C) are used, these are preferably siloxanes composed of units of the general formulae (VII), (VIII) and (IX)

where
  $R^7$ and $R^8$ are as defined above,
  g is 0, 1, 2 or 3,
  h is 0, 1 or 2 and
  i is 0, 1 or 2,
with the proviso that at least two radicals $R^8$ and at least two Si-bonded hydrogen atoms are present per molecule.

Examples of organopolysiloxanes (C) are siloxanes comprising SiO$_{4/2}$, $R^7_3$SiO$_{1/2}$—, $R^7_2R^8$SiO$_{1/2}$— and $R^7_2$HSiO$_{1/2}$— units, known as MP resins, with these resins additionally being able to contain $R^7$SiO$_{3/2}$— and $R^7_2$SiO— units, and also linear organopolysiloxanes consisting essentially of $R^7_2R^8$SiO$_{1/2}$—, $R^7_2$SiO— and $R^7$HSiO— units, where $R^7$ and $R^8$ are as defined above.

The organopolysiloxanes (C) preferably have an average viscosity of from 0.01 to 500,000 Pa·s, more preferably from 0.1 to 100,000 Pa·s, in each case at 25° C., and can be prepared by methods customary in chemistry.

Apart from the abovementioned components (A), (B), (C) and (D), further components (E) or (F) can also be present in the silicone compositions of the invention.

Components (E) such as inhibitors and stabilizers serve to set the processing time, the start behavior and the crosslinking rate of the silicone compositions of the invention in a targeted manner. These inhibitors and stabilizers are very well known in the field of addition-crosslinking compositions. Examples of customary inhibitors are acetylenic alcohols such as 1-ethynyl-1-cyclohexanol, 2-methyl-3-butyn-2-ol and 3,5-dimethyl-1-hexyn-3-ol, 3-methyl-1-dodecyn-3-ol, polymethylvinylcyclosiloxanes such as 1,3,5,7-tetra-vinyltetramethyltetracyclosiloxane, low molecular weight silicone oils having methylvinyl-SiO$_{1/2}$ groups and/or R$_2$vinylSiO$_{1/2}$ end groups, e.g. divinyltetramethyldisiloxane, tetravinyldimethyldisiloxane, trialkyl cyanurates, alkyl maleates such as diallyl maleates, dimethyl maleate and diethyl maleate, alkyl fumarates such as diallyl fumarate and diethyl fumarate, organic hydroperoxides such as cumene hydroperoxide, tert-butyl hydroperoxide and pinane hydroperoxide, organic peroxides, organic sulfoxides, organic amines, diamines and amides, phosphanes and phosphites, nitriles, triazoles, diaziridines and oximes. The action of these inhibitor additives (E) depends on their chemical structure, so that the concentration has to be determined individually. Inhibitors and inhibitor mixtures are preferably added in a proportion of from 0.00001% to 5%, based on the total weight of the mixture, more preferably from 0.00005 to 2% and most preferably from 0.0001 to 1%.

Components (F) are all further additives which are useful for producing addition-crosslinkable compositions. Examples of reinforcing fillers which can be used as component (F) in the silicone compositions of the invention are pyrogenic or precipitated silicas having BET surfaces areas of at least 50 m$^2$/g or preferably in the range from 100 to 400 m$^2$/g as determined by the BET method, and also carbon blacks and activated carbons such as furnace black and acetylene black, with preference being given to pyrogenic and precipitated silicas having BET surface areas of at least 50 m$^2$/g. The silica fillers mentioned can have hydrophilic character or can have been hydrophobicized by known methods. When hydrophilic fillers are mixed in, the addition of a hydrophobicizing agent is necessary. The content of actively reinforcing filler (F) in the crosslinkable composition of the invention is in the range from 0 to 70% by weight, preferably from 0 to 50% by weight.

The silicone composition of the invention can, if desired, contain further additives in a proportion of up to 70% by weight, preferably from 0.0001 to 40% by weight, as constituent (F). These additives can be, for example, inactive fillers, resin-like polyorgano-siloxanes which are different from the siloxanes (A), (B) and (C), reinforcing and nonreinforcing fillers, fungicides, fragrances, rheological additives, corrosion inhibitors, oxidation inhibitors, light stabilizers, flame retardants and agents for influencing the electrical properties, dispersants, solvents, bonding agents, pigments, dyes, plasticizers, organic polymers, heat stabilizers, etc. These include additives such as activated carbon, quartz flour, diatomaceous earth, clays, chalk, lithopones, carbon blacks, graphite, metal oxides, metal carbonates, metal sulfates, metal salts of carboxylic acids, metal dusts, fibers such as glass fibers, polymer fibers, polymer powders, metal dusts, dyes, pigments, etc.

The silicone compositions of the invention can, if necessary, be dissolved, dispersed, suspended or emulsified in liquids.

The compositions of the invention can, particularly as a function of the viscosity of the constituents and the filler content, be of low viscosity or be castable, have a paste-like consistency, be pulverulent or else be malleable, highly viscous compositions as can, as is known, be the case for the compositions frequently referred to in the art as RTV-1, RTV-2, LSR and HTV. In particular, the compositions of the invention can, if they are of high viscosity, be converted into a granular material. Here, the individual granules can contain all components or the components used according to the invention can be incorporated separately in different granules. As regards the elastomeric properties of the crosslinked silicone compositions of the invention, the entire range from extremely soft silicone gels, through rubber-like materials to highly crosslinked silicones having vitreous behavior is likewise encompassed.

The production of the silicone compositions of the invention can be carried out by known methods, for example by homogeneous mixing of the individual components, for example by mixing either
- at least one compound of each of (A), (B) and (D), or
- at least one compound of each of (C) and (D), or
- at least one compound of each of (A), (B), (C) and (D), or
- at least one compound of each of (A), (C) and (D), with one another in any order.

The order is immaterial, but preference is given to homogeneously mixing the platinum catalyst (D) with a mixture of (A), (B) and, if used, (E) and (F). The platinum catalyst (D) used according to the invention can be incorporated as such or as a solution dissolved in a suitable solvent or as masterbatch mix homogeneously with a small amount of (A) or (A) together with (E).

The components (A) to (F) used according to the invention can in each case be a single type of such a component or a mixture of at least two different types of such a component.

The silicone compositions of the invention which can be crosslinked by addition of Si-bonded hydrogen onto aliphatic multiple bonds can be crosslinked under the same conditions as the previously known compositions which can be crosslinked by means of a hydrosilylation reaction.

The addition-crosslinking silicone compositions of the invention can contain further catalysts (G) which can bring about crosslinking, for instance hydrosilylation catalysts, peroxides, cationic or anionic crosslinkers or condensation crosslinkers.

The present invention further provides moldings produced by crosslinking the silicone compositions of the invention.

The silicone compositions of the invention and the crosslinking products produced therefrom according to the invention can be used for all purposes for which organopolysiloxane compositions which can be crosslinked to form elastomers or elastomers have hitherto also been used. This encompasses, for example, silicone-coating or impregnation of any substrates, the production of moldings, for example by injection molding, vacuum extrusion, extrusion, casting in a mold and compression molding and taking casts, the use as sealing compositions, embedding compositions and potting compounds, etc.

The crosslinkable silicone compositions of the invention have the advantage that they can be produced in a simple process using readily available starting materials and thus economically. The crosslinkable compositions of the invention have the further advantage that they have a good storage stability as a one-component formulation at 25° C. and ambient pressure and crosslink only on irradiation with visible or ultraviolet radiation. The crosslinking time is dependent on the duration and intensity of irradiation.

The silicone compositions of the invention have the advantage that in the case of a two-component formulation they give, after mixing of the two components, a crosslinkable silicone composition whose processability is maintained over a long period at 25° C. and ambient pressure, i.e. display extremely long pot lives, and crosslink only on irradiation.

In the production of the crosslinkable compositions of the invention, it is a great advantage that the platinum catalyst (D) can be readily metered and easily incorporated.

The compositions of the invention have the further advantage that the crosslinked silicone rubbers obtained therefrom display excellent transparency.

The compositions of the invention also have the advantage that the hydrosilylation reaction does not become slower with increasing reaction time and does not necessarily stop when irradiation is stopped. Regions which have not been directly illuminated also cure, which is particularly advantageous in the case of true-to-detail casts or in the casting of electronic components. Crosslinking cannot be initiated but can be accelerated by increasing the temperature.

Crosslinked silicone elastomers of the invention are obtained by light-induced addition crosslinking of the compositions of the invention. Here, the crosslinking reaction is carried out by methods known to those skilled in the art.

In the following, the term organopolysiloxanes encompasses polymeric, oligomeric and also dimeric siloxanes.

EXAMPLES

In the examples described below, all parts and percentages are, unless indicated otherwise, by weight. Unless indicated otherwise, the following examples are carried out at the pressure of the surrounding atmosphere, i.e. at about 1000 hPa, and at room temperature, i.e. at about 20° C., or at a temperature which is established on combining the reactants at room temperature without additional heating or cooling. All viscosities reported below are based on a temperature of 25° C. The following examples illustrate the invention without having a limiting effect.

The following abbreviations are used:

| | |
|---|---|
| Cat. | Platinum catalyst |
| Ex. | Example |
| No. | Number |

Example 1

Preparation of the Cyclopentadienyl-Functionalized Silane 1

27.5 g (417 mmol) of freshly distilled cyclopentadiene are added dropwise to a suspension of 15 g (417 mmol) of sodium hydride in 250 ml of absolute tetrahydrofuran at room temperature over a period of one hour. 100.3 g of (3-chloropropyl)triethoxysilane are subsequently added dropwise over a period of 30 minutes. The solution becomes warm during this process. After taking off the solvent, the mixture is fractionally distilled in an oil pump vacuum to give 96.1 g of (3-cyclopenta-dienylpropyl)triethoxysilane (yield: 90%).

Example 2

Preparation of the Cyclopentadienyl-Functionalized Silane 2

27.5 g (417 mmol) of freshly distilled cyclopentadiene are added dropwise to a suspension of 10 g (417 mmol) of sodium hydride in 250 ml of absolute tetrahydrofuran at room temperature over a period of one hour. 76.1 g of (3-chloropropyl)dimethoxymethylsilane are subsequently added dropwise over a period of 30 minutes. The solution becomes warm during this process. After taking off the solvent, the mixture is fractionally distilled in an oil pump vacuum to give 68.6 g of (3-cyclopentadienylpropyl)dimethoxy-methylsilane (yield: 83%).

Example 3

Preparation of the Cyclopentadienyl-Functionalized Silane 3

33.4 g (417 mmol) of freshly distilled methylcyclopentadiene are added dropwise to a suspension of 10 g (417 mmol) of sodium hydride in 250 ml of absolute diethyl ether at RT over a period of one hour. 76.1 g of (3-chloropropyl)dimethoxy-methylsilane are subsequently added dropwise over a period of 30 minutes. The solution becomes warm during this process. After taking off the solvent, the mixture is fractionally distilled in an oil pump vacuum to give 78.9 g of (3-methylcyclopentadienylpropyl)dimethoxy-methylsilane (yield: 89%).

Example 4

Preparation of the Cyclopentadienyl-Functionalized Silane 4

27.5 g (417 mmol) of freshly distilled cyclopentadiene are added dropwise to a solution of 167 ml of n-butyllithium (2.5 molar) (417 mmol) in 250 ml of absolute tetrahydrofuran at RT over a period of one hour. 71.11 g of (chloromethyl)trimethoxysilane are subsequently added dropwise over a period of 30 minutes. The solution becomes warm during this process. After taking off the solvent, the mixture is fractionally distilled under reduced pressure to give 72.2 g of (cyclopentadienylmethyl)trimethoxysilane (yield: 93%).

Example 5

Preparation of Monomeric Platinum Compound 0.72 g of sodium hydride is added to a solution of 7.0 g of silane 1 in 50 ml of absolute tetrahydrofuran. 10 g of trimethylplatinum(IV) iodide (27.2 mmol) are added to this and the mixture is stirred at room temperature for two hours. After taking off the solvent, the platinum compound is purified by distillation under reduced pressure. This gives 12.3 g of pure trimethyl[(3-triethoxysilyl)propylcyclopenta-dienyl]platinum(IV).

Example 6

Preparation of Monomeric Platinum Compound 2

0.72 g of sodium hydride is added to a solution of 5.4 g of silane 2 in 50 ml of absolute tetrahydrofuran. 10 g of trimethylplatinum(IV) iodide (27.2 mmol) are added to this and the mixture is stirred at room temperature for two hours. After taking off the solvent, the platinum compound is purified by distillation under reduced pressure. This gives 11.2 g of pure trimethyl[(3-dimethoxymethylsilyl)propyl-cyclopentadienyl]platinum(IV).

Example 7

Preparation of Monomeric Platinum Compound 3

0.72 g of sodium hydride is added to a solution of 5.8 g of silane 3 in 50 ml of absolute tetrahydrofuran. 10 g of trimethylplatinum(IV) iodide (27.2 mmol) are added to this and the mixture is stirred at room temperature for two hours. After taking off the solvent, the platinum compound is purified by distillation under reduced pressure. This gives 11.5 g of pure trimethyl[(3-dimethoxymethylsilyl)propyl-methylcyclopentadienyl]platinum(IV).

Example 8

Preparation of Monomeric Platinum Compound 4

12.0 ml of a 2.5 molar butyllithium solution are added to a solution of 5.1 g of silane 4 in 50 ml of absolute tetrahydrofuran. 10 g of trimethylplatinum(IV) iodide (27.2 mmol) are added to this and the mixture is stirred at room temperature for two hours. After taking off the solvent, the platinum compound is purified by distillation under reduced pressure. This gives 10.3 g of pure trimethyl[(trimethoxysilyl)methylcyclopenta-dienyl]platinum(IV).

Example 9

Comparative Example, Platinum Compound 5

The commercially available platinum compound trimethyl(methylcyclopentadienyl)platinum(IV), which is used directly as catalyst, serves as comparative example. It bears no further functional groups and consequently cannot be crosslinked into the siloxane matrix.

Examples of the cohydrolysis of the platinum compounds with siloxanes follow. All starting materials known to those skilled in the art (monomers, oligomers, polymers and the associated catalysts) which are used in condensation systems can be employed for the reaction.

Example 10

Cohydrolysis of Platinum Compound 1 from Example 5

A mixture of 2.54 g of platinum compound 1, 97.46 g of α,ω-silanol-terminated polydimethylsiloxane [CAS 70131-67-8] having a viscosity of 1000 mPa·s and 0.025 g of aluminum tris(2,4-pentanedionate) is prepared at 25° C. and stirred at room temperature for 24 hours.

Example 11

A mixture of 2.24 g of platinum compound 2, 97.46 g of α,ω-silanol-terminated polydimethylsiloxane [CAS 70131-67-8] having a viscosity of 1000 mPa·s and 0.025 g of Zn(acac)$_2$ is prepared at 50° C. and stirred at room temperature for 24 hours.

Example 12

A mixture of 2.31 g of platinum compound 3, 97.46 g of α,ω-silanol-terminated polydimethylsiloxane [CAS 70131-67-8] having a viscosity of 1000 mPa·s and 0.025 g of Zn(acac)$_2$ is prepared at 50° C. and stirred at room temperature for 24 hours.

Example 13

A mixture of 2.18 g of platinum compound 4, 97.46 g of α,ω-silanol-terminated polydimethylsiloxane [CAS 70131-67-8] having a viscosity of 1000 mPa·s and 0.025 g of butyllithium is prepared and stirred at room temperature for 24 hours.

TABLE 1

| Ex. No. | Cat. from Ex. No. | Dark reactivity [h] 22° C. | Dark reactivity [h] 120° C. | Gel time after illumination[1] |
|---|---|---|---|---|
| 15 | 9 | 1300 | 1.5 | 120 |
| 16 | 10 | >1500 | 2 | 104 |
| 17 | 11 | >1500 | 3.2 | 93 |
| 18 | 12 | >1500 | 2.5 | 125 |
| 19 | 13 | >1500 | 3 | 108 |

[1]illumination for 10 seconds in a UV cube from Höhnle (about 70 mW/cm$^2$) by means of an iron lamp having a wavelength of 230-400 nm.

Table 1 shows the results from the determination of the dark reactivity and gel time after illumination for selected examples.

The invention claimed is:

1. A platinum compound of the formula (I)

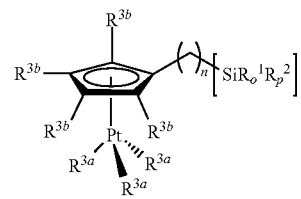

(I)

where n=1 to 8, o=0 to 2, p=1 to 3, and the sum of o and p is 3, and the radicals $R^1$ are identical or different and are each, independently of one another, a monovalent, unsubstituted or substituted, linear, cyclic or branched hydrocarbon radical which contains aliphatically saturated or unsaturated or aromatically unsaturated radicals and has from 1 to 30 carbon atoms and in which individual carbon atoms are optionally replaced by O, N, S or P atoms, the radicals $R^2$ are identical or different and are each, independently of one another, hydrolyzable functional groups selected from the group consisting of carboxy —O—C(O)$R^4$, oxime —O—N=$CR^4{}_2$, alkoxy —O$R^4$, alkenyloxy —O—$R^6$, amide —N$R^4$—C(O)$R^5$, amine —N$R^4R^5$, aminoxy —O—N$R^4R^5$, where the radicals $R^4$ are identical or different and are each, independently of one another, H, alkyl, aryl, arylalkyl, or alkylaryl, the radicals $R^5$ are identical or different and are each, independently of one another, alkyl, aryl, arylalkyl, or alkylaryl, $R^6$ is a linear or branched, aliphatically unsaturated organic radical, the radicals $R^{3a}$ are identical or different and are each, independently of one another, alkyl, aryl, arylalkyl, or alkylaryl, the radical $R^{3a}$ having from 1 to 30 carbon atoms, where hydrogens in the radical $R^{3a}$ are optionally substituted by -Hal or —Si$R_3{}^3$, where the radicals $R^3$ are identical or different and are each, independently of one another, a monovalent, unsubstituted or substituted, linear, cyclic or branched hydrocarbon radical, the radicals $R^{3b}$ are identical or different and are each, independently of one another, hydrogen or a monovalent, unsubstituted or substituted, linear or branched hydrocarbon radical which contains aliphatically saturated or unsaturated or aromatically unsaturated radicals and has from 1 to 30 carbon atoms and in which individual carbon atoms are optionally replaced by O, N, S or P atoms, or of the formula II

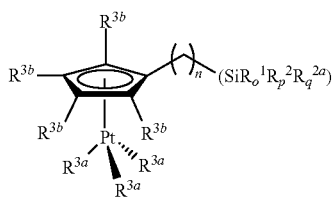

(II)

where
R¹, R², R³, R³ᵃ and R³ᵇ, n, o, p are as defined above,
q=1 to 3, and
the sum of o, p, and q is 3, and
the radicals R²ᵃ are identical or different and are each, independently of one another, a monovalent, linear, cyclic or branched, monomeric, oligomeric or polymeric organosiloxy radical which optionally contains one or more of
a) aliphatically saturated groups which have from 1 to 30 carbon atoms and in which individual carbon atoms may be replaced by Hal, O, N, S or P atoms,
b) aliphatically unsaturated groups which have from 1 to 30 carbon atoms and in which individual carbon atoms may be replaced by Hal, O, N, S or P atoms,
c) aromatic groups which have from 1 to 30 carbon atoms and in which individual carbon atoms may be replaced by Hal, O, N, S or P atoms,
d) Si-bonded hydrogen atoms,
e) hydroxyl groups, and
f) hydrolyzable groups.

2. A process for preparing a platinum compound of the formula (I) of claim 1, comprising reacting a platinum precursor with a monomeric cyclopentadienyl-alkylsilane containing at least one hydrolyzable group, in an aprotic solvent at a temperature of from −78° C. to 150° C.

3. A platinum catalyst (D) of claim 1 of the formula (II)

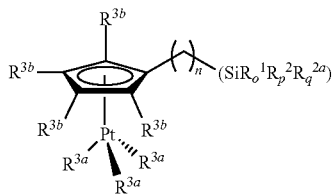

(II)

where
R¹, R², R³, R³ᵃ and R³ᵇ, n, o, p are as defined above,
q=1 to 3, and
the sum of o, p, and q is 3, and
the radicals R²ᵃ are identical or different and are each, independently of one another, a monovalent, linear, cyclic or branched, monomeric, oligomeric or polymeric radical which optionally contains one or more of
a) aliphatically saturated groups which have from 1 to 30 carbon atoms and in which individual carbon atoms may be replaced by Hal, O, N, S or P atoms,
b) aliphatically unsaturated groups which have from 1 to 30 carbon atoms and in which individual carbon atoms may be replaced by Hal, O, N, S or P atoms,
c) aromatic groups which have from 1 to 30 carbon atoms and in which individual carbon atoms may be replaced by Hal, O, N, S or P atoms,
d) Si-bonded hydrogen atoms,
e) hydroxyl groups, and
f) hydrolyzable groups.

4. The platinum catalyst (D) of claim 3, which has a molecular weight of at least 500 g/mol.

5. A process for preparing a platinum catalyst comprising cohydrolyzing a platinum compound of the formula (I)

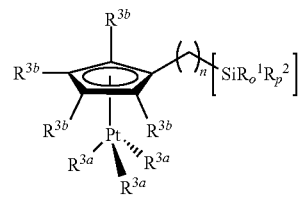

(I)

where
n=1 to 8,
o=0 to 2,
p=1 to 3, and
the sum of o and p is 3, and
the radicals $R^1$ are identical or different and are each, independently of one another, a monovalent, unsubstituted or substituted, linear, cyclic or branched hydrocarbon radical which contains aliphatically saturated or unsaturated or aromatically unsaturated radicals and has from 1 to 30 carbon atoms and in which individual carbon atoms are optionally replaced by O, N, S or P atoms,
the radicals $R^2$ are identical or different and are each, independently of one another, hydrolyzable functional groups selected from the group consisting of
carboxy —O—C(O)R⁴,
oxime —O—N═CR⁴₂,
alkoxy —OR⁴,
alkenyloxy —O—R⁶,
amide —NR⁴—C(O)R⁵,
amine —NR⁴R⁵,
aminoxy —O—NR⁴R⁵, where
the radicals $R^4$ are identical or different and are each, independently of one another, H, alkyl, aryl, arylalkyl, or alkylaryl,
the radicals $R^5$ are identical or different and are each, independently of one another, alkyl, aryl, arylalkyl, or alkylaryl,
$R^6$ is a linear or branched, aliphatically unsaturated organic radical,
the radicals $R^{3a}$ are identical or different and are each, independently of one another, alkyl, aryl, arylalkyl, or alkylaryl, the radical $R^{3a}$ having from 1 to 30 carbon atoms, where hydrogens in the radical $R^{3a}$ are optionally substituted by -Hal or —SiR₃³, where
the radicals $R^3$ are identical or different and are each, independently of one another, a monovalent, unsubstituted or substituted, linear, cyclic or branched hydrocarbon radical,
the radicals $R^{3b}$ are identical or different and are each, independently of one another, hydrogen or a monovalent, unsubstituted or substituted, linear or branched hydrocarbon radical which contains aliphatically saturated or unsaturated or aromatically unsaturated radicals and has from 1 to 30 carbon atoms and in which individual carbon atoms are optionally replaced by O, N, S or P atoms, or of the formula II

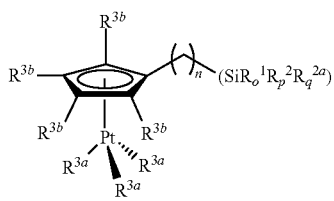

(II)

where
R$^1$, R$^2$, R$^3$, R$^{3a}$ and R$^{3b}$, n, o, p are as defined above,
q=1 to 3, and
the sum of o, p, and q is 3, and
the radicals R$^{3a}$ are identical or different and are each, independently of one another, a monovalent, linear, cyclic or branched, monomeric, oligomeric or polymeric organosilicon radical which optionally contains one or more of
a) aliphatically saturated groups which have from 1 to 30 carbon atoms and in which individual carbon atoms may be replaced by Hal, O, N, S or P atoms,
b) aliphatically unsaturated groups which have from 1 to 30 carbon atoms and in which individual carbon atoms may be replaced by Hal, O, N, S or P atoms,
c) aromatic groups which have from 1 to 30 carbon atoms and in which individual carbon atoms may be replaced by Hal, O, N, S or P atoms,
d) Si-bonded hydrogen atoms,
e) hydroxyl groups, and
f) hydrolyzable groups
with at least one organosilicon compound.

6. A hydrosilylation reaction, a hydrogenation of unsaturated compounds, or a polymerization reaction, containing at least one platinum catalyst (D) of claim 3 which activates the reaction by ultraviolet or visible radiation.

7. An addition-crosslinking silicone rubber composition, comprising
(i) at least one of compounds (A), (B) and (C), where
(A) is an organic or organosilicon compound containing at least two radicals having aliphatic carbon-carbon multiple bonds,
(B) is an organosilicon compound containing at least two Si-bonded hydrogen atoms, and
(C) is an organosilicon compound containing SiC-bonded radicals having aliphatic carbon-carbon multiple bonds and Si-bonded hydrogen atoms,
with the proviso that the composition contains at least one compound having aliphatic carbon-carbon multiple bonds and at least one compound having Si-bonded hydrogen atoms,
and
(ii) at least one platinum catalyst (D) of claim 3.

8. The silicone rubber composition of claim 7, further comprising at least one inhibitor or stabilizer as further constituent(s) (E), in a proportion of from 0.00001% to 5%, based on the total weight of the composition.

9. The silicone rubber composition of claim 7, further comprising, as at least one further constituent, at least one constituent (F) selected from the group consisting of reinforcing and nonreinforcing fillers, dispersants, solvents, bonding agents, pigments, dyes, plasticizers, organic polymers, heat stabilizers, fungicides, fragrances, rheological additives, corrosion inhibitors, oxidation inhibitors, light stabilizers, flame retardants and agents for influencing electrical properties.

10. A process for producing a silicone rubber composition of claim 7, comprising admixing
at least one compound of each of (A), (B) and (D), or
at least one compound of each of (C) and (D), or
at least one compound of each of (A), (B), (C) and (D), or
at least one compound of each of (A), (C) and (D).

11. A crosslinked silicone elastomer obtained by light-induced addition crosslinking of a silicone rubber composition of claim 7.

* * * * *

UNITED STATES PATENT AND TRADEMARK OFFICE
CERTIFICATE OF CORRECTION

PATENT NO. : 8,088,878 B2  Page 1 of 1
APPLICATION NO. : 12/863521
DATED : January 3, 2012
INVENTOR(S) : Andreas Koellnberger It is certified that error appears in the above-identified patent and that said Letters Patent is hereby corrected as shown below:

Column 21, Line 57, Claim 2:

After "oligomeric or polymeric"
Insert -- organosiloxy --.

Column 23, line 17, Claim 5:

Delete: "$R^{3a}$", Insert: -- $R^{2a}$ --.

Signed and Sealed this
Twentieth Day of March, 2012

David J. Kappos
*Director of the United States Patent and Trademark Office*